US00PP37565P3

(12) United States Plant Patent
Elstgeest

(10) Patent No.: US PP37,565 P3
(45) Date of Patent: Aug. 4, 2026

(54) ***ALOCASIA* PLANT NAMED 'ELSTCIRCU'**

(50) Latin Name: *Alocasia wentii*
Varietal Denomination: 'ELSTCIRCU'

(71) Applicant: ELSTGEEST YOUNG PLANTS HOLDING B.V., Rijsenhout (NL)

(72) Inventor: Debbie Elstgeest, Rijsenhout (NL)

(73) Assignee: Elstgeest Young Plant Holding BV, Rijsenhout (NL)

( * ) Notice: Subject to any disclaimer, the term of this patent is extended or adjusted under 35 U.S.C. 154(b) by 0 days.

(21) Appl. No.: 19/347,027

(22) Filed: Oct. 1, 2025

(65) Prior Publication Data

US 2026/0157252 P1 Jun. 4, 2026

(30) Foreign Application Priority Data

Dec. 4, 2024 (QZ) ..... PBR 2024/3004

(51) Int. Cl.
*A01H 5/12* (2018.01)
*A01H 6/10* (2018.01)

(52) U.S. Cl.
USPC ..... Plt./373
CPC ..... *A01H 6/10* (2018.05); *A01H 5/12* (2013.01)

(58) Field of Classification Search
USPC ..... Plt./373
CPC ..... A01H 5/12; A01H 5/00; A01H 6/10
See application file for complete search history.

*Primary Examiner* — June Hwu
(74) *Attorney, Agent, or Firm* — James R. Holm; Plant Novelty Rights, LLC

(57) ABSTRACT

A new and distinct *Alocasia* plant named 'ELSTCIRCU' particularly distinguished by a unique and irregular leaf variegation color pattern consisting of marbled and blotched tones of green, yellow-green, greyed-green, yellow and white; large, pointed leaves with strong vertical presentation; and a broad, upright and vigorous growth habit with elongated petioles and an open architecture.

3 Drawing Sheets

Figure 1:
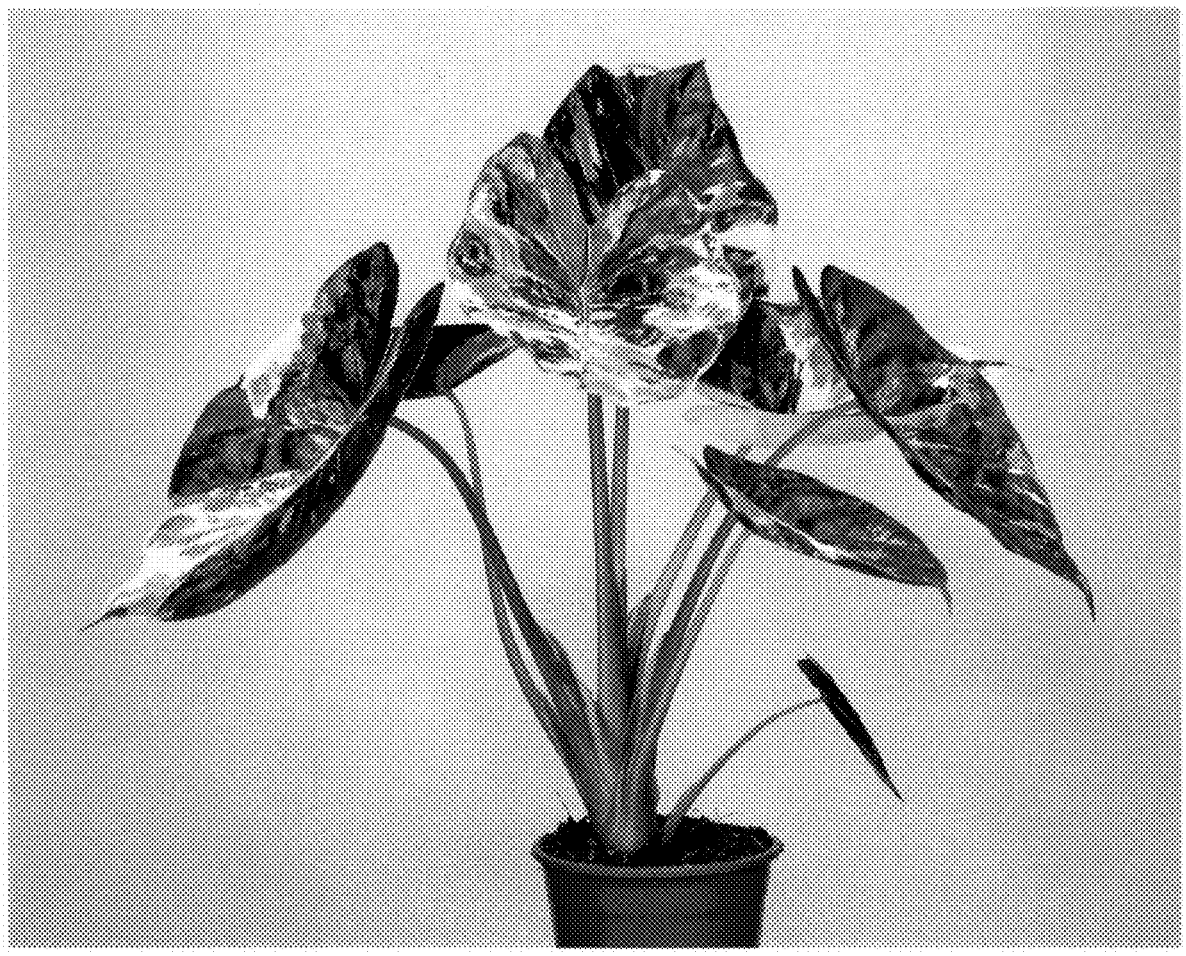

Genus and species: *Alocasia wentii.*
Variety denomination: 'ELSTCIRCU'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date. This application claims priority to CPVO application no. 2024/3004 filed on Dec. 4, 2024.

BACKGROUND OF THE NEW PLANT

The present invention comprises a new and distinct variety of *Alocasia* plant, botanically known as *Alocasia wentii*, and hereinafter referred to by the variety name 'ELSTCIRCU'. The new *Alocasia* cultivar is a product of a planned breeding program located in Rijsenhout, The Netherlands. The new cultivar is a naturally occurring branch mutation originating from an unnamed and unpatented population of *Alocasia wentii* plants cultivated in a greenhouse in Rijsenhout, The Netherlands. Several mutations were selected by the inventor from said population of *Alocasia wentii* plants for a period of 1 month. The mutations were grown in 14 cm pots and observed for uniformity, stability, and distinctness as well as for their commercial potential. From amongst these mutations, 'ELSTCIRCU' was selected by the inventor in May 2022 for further propagation and commercialization based on its unique leaf color pattern consisting of five colorations.

The new *Alocasia* cultivar 'ELSTCIRCU' was first reproduced asexually using meristematic tissue culture in May 2023 in Rijsenhout, The Netherlands. Asexual propagation by meristematic tissue culture of the new variety has shown that the unique features of the new variety are stable and reproduced true-to-type to date through 8 successive generations.

SUMMARY OF THE INVENTION

The new *Alocasia* cultivar 'ELSTCIRCU' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'ELSTCIRCU' as a new and distinct variety of *Alocasia.*

1. *Alocasia* 'ELSTCIRCU' exhibits a unique and irregular leaf variegation color pattern on the upper surface of mature leaves consisting of marbled and blotched tones of green, yellow-green, greyed-green, yellow and white.
2. *Alocasia* 'ELSTCIRCU' exhibits large, pointed leaves with strong vertical orientation.
3. *Alocasia* 'ELSTCIRCU' exhibits a broad, upright and vigorous growth habit with elongated petioles and an open architecture.

The new *Alocasia* cultivar can be distinguished from its progenitor or parent species *Alocasia wentii* by having variegated leaves mottled and marbled in various tones of green, yellow-green, greyed-green, yellow and white, whereas the progenitor or parent species *Alocasia wentii* has leaves that are solid green with no variegation.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are 20-week-old plants grown in 14-centimeter circular containers in a conventional glass greenhouse in Rijsenhout, The Netherlands. Colors in the photographs may differ slightly from the color values cited in the botanical description which accurately describes the colors of the new variety.

FIG. 1. shows the overall plant form and foliage of 'ELSTCIRCU'.

Figure 2:
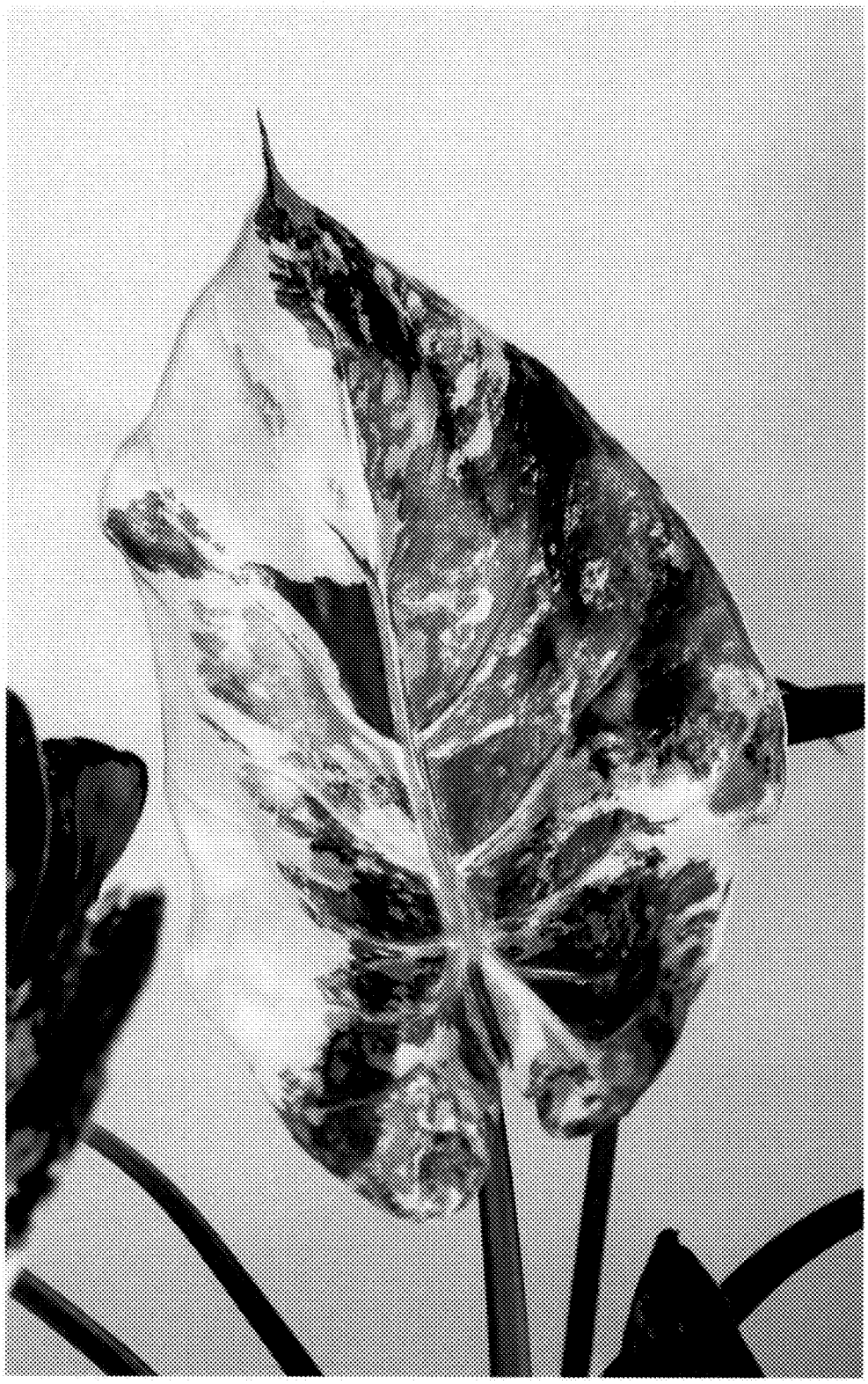

FIG. 2. shows a close-up of a typical immature leaf of 'ELSTCIRCU'.

Figure 3:
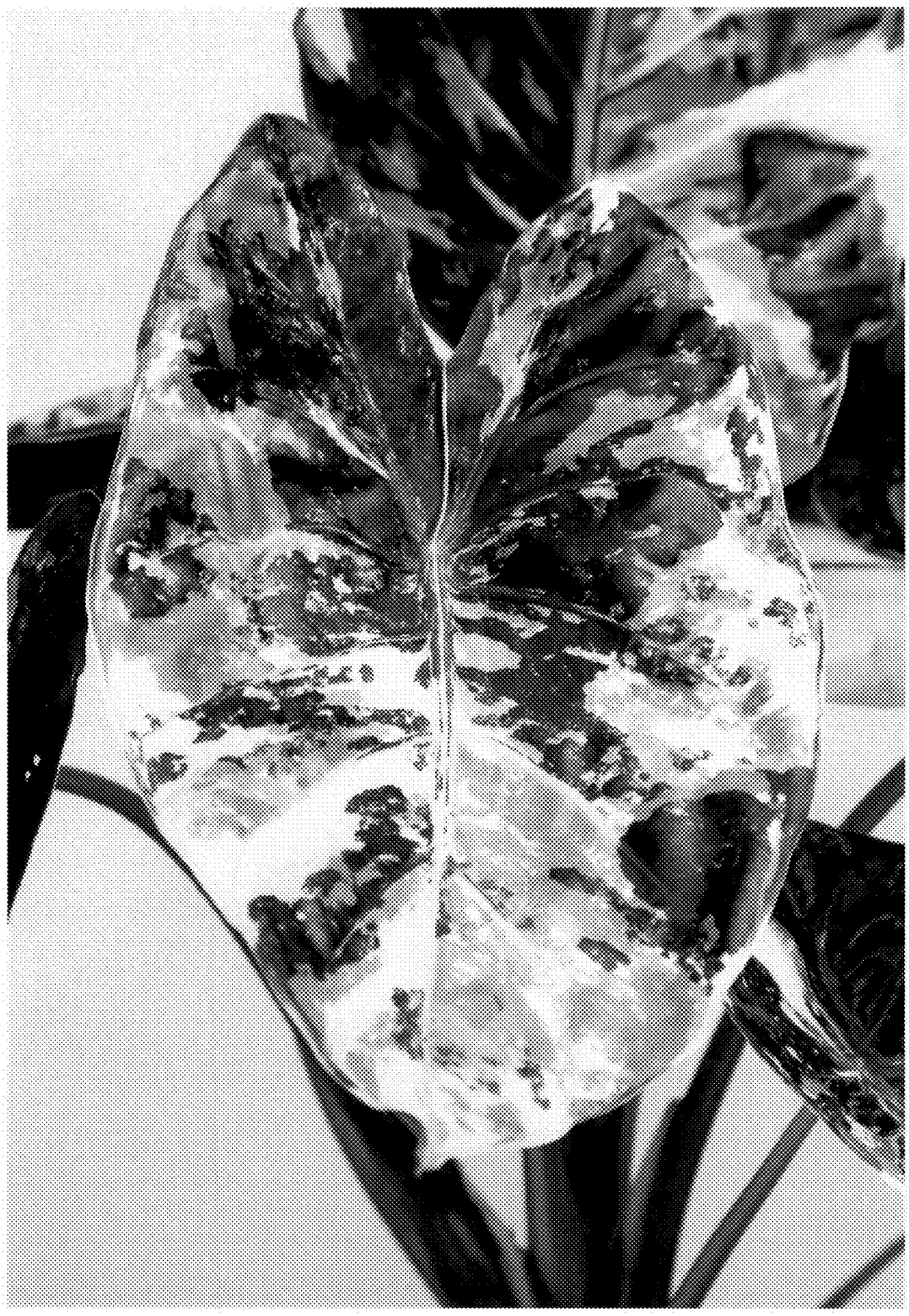

FIG. 3. shows a close-up of a typical mature leaf of 'ELSTCIRCU'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional glass greenhouse located in Rijsenhout, The Netherlands. Growing condition consisted of an average day and night temperature of 20° C. to 22° C., 60 to 85 percent relative humidity, 150-200 μmol/m$^2$/sec (PAR) of light, and 600 to 700 ppm of CO2. Detailed descriptions were taken in November 2024 from 20-week-old plants grown in 14-centimeter circular containers. Measurements and numerical values represent averages of typical plant types.

DETAILED BOTANICAL DESCRIPTION

Classification:

*Family*.—Araceae.

*Botanical*.—*Alocasia wentii*.

*Denomination*.—'ELSTCIRCU'.

General description:

*Plant type*.—Tropical perennial for use as a potted ornamental plant.

*Approximate container size and/or cropping system*.—12.0 cm or larger pots.

*Growth habit*.—Broad and upright.

*Overall plant shape*.—Broadly obovate.

*Height from soil level to top of foliar plane*.—43.1 cm.

*Plant diameter or area of spread*.—53.0 cm.

*Growth rate*.—Moderate.

*Plant vigor*.—Moderate.

*Branching habit*.—Growth emerges from basal clumps.

*Stem description*.—Stemless.

*Quantity of divisions or clumps per plant*.—1.

*Propagation type*.—Meristematic tissue culture.

Foliage description:

*Arrangement*.—Alternate, simple.

*Quantity of leaves per basal clump*.—Average of 8.

*Lamina*.—Shape: Ovate to broadly ovate. Length: Average 26.4 cm. Width: Average 15.7 cm. Aspect: Slightly to moderately concave. Apex shape: Apiculate to aristate. Base shape: Cordate to hastate. Margins: Entire, slightly repand, and slightly coarsely undulate. Texture (both upper and lower surfaces): Smooth, glabrous, and leathery. Pubescence: Not present. Luster: Upper surface: Very slightly glossy. Lower surface: Slightly glossy. Color: Juvenile foliage: Upper surface: 146A (green), heavily and irregularly blotched and marbled with 146B (light yellow-green), a blend of N187C of N187D (greyed-purple), a blend of N187C (greyed-purple) and 198A (greyed-green), and a blend of 39D (red) and N170D (greyed-orange). Lower surface: N77A (purple), heavily and irregularly blotched and marbled with N77D (light purple), a blend of N77D (light purple) and N187C (greyed-purpled), a blend of N187C (greyed-purple) and 189A (greyed-green), 182D (greyed-red), and N155C (white). Mature foliage: Upper surface: A blend of 147A (yellow-green) and 189A (greyed-green), heavily and irregularly blotched and marbled with 146A and 147A (yellow-green), 189A (greyed-green), 198C (greyed-green), a blend of 155A (white) and 4D (yellow), and 4D (yellow). Lower surface: A blend of N189A (greyed-green) and 200A (brown) and slightly darker than 200A, heavily and irregularly blotched and marbled with 194A (greyed-green), 194B (greyed-green), a blend of 155A (white) and 4D (yellow), and the 194A and 194B (greyed-green) areas slightly flushed with 182C (greyed-red). Venation: Pattern: Pinnate. Color (mature leaves): Upper surface: A blend of 147A (yellow-green) and N189A (greyed-green), but in tones slightly lighter than the leaf colorations, and slightly to heavily striped 193D (greyed-green). Lower surface: 148A (yellow-green) and slightly to heavily striped lighter with N148B (yellow-green); secondary veins colored a blend of N189A (greyed-green) and 200A (brown).

*Petiole*.—Length: 30.7 cm. Diameter: 1.3 cm at the proximal end and 0.6 cm at the distal end. Texture: Smooth, glabrous. Luster (both upper and lower surfaces): Matte. Strength: Strong. Color: Upper surface: NN137C (green), and main vein colored 190A (greyed-green). Lower surface: 148B (yellow-green), axillary striped 193A (greyed-green). Wings: Length: Average 13.7 cm. Width: Average 1.6 cm. Color: Inner surface: 148C (yellow-green), tinged 197A (greyed- green), and irregularly blotched N155D (white). Outer surface: 148B and 148C (yellow-green), tinged 197A (greyed-green), and irregularly blotched N155C and N155D (white).

Inflorescence: None observed to date.

High temperature tolerance: Up to 40 degrees Celsius.

Low temperature tolerance: Down to greater than 5 degrees Celsius.

USDA hardiness zones: Zones 10 to 13.

Rain tolerance: Moderate to high.

Wind tolerance: Low.

Disease and pest tolerance: No claims are made to any superior disease or insect resistance or tolerance.

COMPARISON WITH RELATED KNOWN VARIETY

The new *Alocasia* cultivar 'ELSTCIRCU' can be distinguished from the related known variety of *Alocasia wentii* cultivar 'Aurea Variegata' (unpatented) in the following characteristics described in Table 1 below.

TABLE 1

| Characteristic | 'ELSTCIRCU' | 'Aurea Variegata' |
|---|---|---|
| Leaf shape. | Ovate to broadly ovate, somewhat narrower and more elongated. | Broadly ovate to cordate, moderately wide with smooth margins. |
| Leaf color (upper surface). | Dark green background with large, irregular variegation of green, yellow-green, greyed-green, yellow and white. | Bright yellow to golden sectors mixed with medium green variegation. |

TABLE 1-continued

| Characteristic | 'ELSTCIRCU' | 'Aurea Variegata' |
|---|---|---|
| Leaf pattern. | Strongly mottled and blotched variegation against a dark green background. | Sectorial and marbled aurea variegation, irregular patches of yellow/gold. |
| Leaf size. | Larger leaves, longer and more pointed. | Medium-sized leaves, generally shorter and broader. |
| Leaf orientation | More upright with a stronger vertical orientation. | Slightly arching and outwardly facing. |
| Petiole color. | Green to grey-green, often darker near the base. | Yellow-green to light green. |
| Growth habit. | More upright and vigorous with elongated petioles and an open architecture. | Compact plant habit with a shorter internode length, and bushier appearance. |

What is claimed is:

1. A new and distinct cultivar of *Alocasia* plant named 'ELSTCIRCU', substantially as illustrated and described herein.

* * * * *